United States Patent
Rita et al.

(10) Patent No.: US 8,048,417 B2
(45) Date of Patent: *Nov. 1, 2011

(54) ANTI-HUMAN TENASCIN MONOCLONAL ANTIBODY

(75) Inventors: De Santis Rita, Rome (IT); Anastasi Anna Maria, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 367 days.

This patent is subject to a terminal disclaimer.

(21) Appl. No.: 12/232,431

(22) Filed: Sep. 17, 2008

(65) Prior Publication Data

US 2011/0020219 A1 Jan. 27, 2011

Related U.S. Application Data

(63) Continuation of application No. 10/505,747, filed on Aug. 25, 2004, now Pat. No. 7,438,908, which is a continuation of application No. PCT/IT2003/00098, filed on Feb. 20, 2003.

(60) Provisional application No. 60/359,299, filed on Feb. 26, 2002.

(51) Int. Cl.
*C07K 16/00* (2006.01)
*G01N 33/53* (2006.01)
*A61K 39/395* (2006.01)

(52) U.S. Cl. ............ 424/134.1; 530/388.24; 530/391.1; 530/391.3; 530/391.7; 435/7.1; 435/810; 435/975; 424/145.1

(58) Field of Classification Search .................... None
See application file for complete search history.

(56) References Cited

U.S. PATENT DOCUMENTS

| | | | |
|---|---|---|---|
| 4,687,732 A | 8/1987 | Ward | |
| 5,482,698 A | 1/1996 | Griffiths | |
| 5,624,659 A | 4/1997 | Bigner et al. | |
| 5,820,858 A | 10/1998 | Leturcq | |
| 5,859,205 A * | 1/1999 | Adair et al. | 530/387.3 |
| 6,335,014 B1 | 1/2002 | Kusakabe | |

FOREIGN PATENT DOCUMENTS

WO 03/075960 9/2003

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Eduardo Padlan, Anatomy of the antibody molecule. Mol Immunol. Feb. 1994;31(3):169-217.*
Klimka et al.,Human anti-CD30 recombinant antibodies by guided phage antibody selection using cell panning. British Journal of Cancer (2000) 83:252-260.*
Beiboer et al.,Guided selection of a pan carcinoma specific antibody reveals similar binding characteristics yet structural divergence between the original murine antibody and its human equivalent. J. Mol., Biol. (2000) 296:833-849).*
Paul, Fundamental Immunology, 3rd Edition, 1993, pp. 292-295.*
Casset et al. A peptide mimetic of an anti-CD4 monoclonal antibody by rational design. Biochem Biophys Res Commun. Jul. 18, 2003;307(1)198-205.*
MacCallum et al. Antibody-antigen interactions: contact analysis and binding site topography. J Mol Biol. Oct. 11, 1996;262(5):732-45.*
Balza et al. "Production and characterization of monoclonal antibodies specific for different epitopes of human tenascin" FEBS Lett. 332:39-43 (1993).
Chinol et al, "Biochemical modifications of avidin improve pharmacokinetics and biodistribution, and reduce immunogenicity" Brit. J. Cancer, 78:189-197 (1998).
Chinol et al. "Biodistribution in tumour-bearing mice of two 90Y-labelled biotins using three-step tumour targeting" Nucl. Med. Commun. 18:176-182 (1997).
Cremonesi et al. "Three-step radioimmunotherapy with Yttrium-90 biotin: Dosimetry and pharmacokinetics in cancer patients" Eur. J. Nucl. Med. 26:110-120 (1999).
De Santis et al. "Novel antitenascin antibody with increased tumour localisation for pretargeted antibody-guided radio immunotherapy (Pagrit)" Brit. J. Cancer 88:996-1003 (2003).
Hart et al. "HPMA copolymer-modified avidin: Immune response" J. Biomaterials Sci. 11:1-12 (2000).
Paganelli et al. "Antibody-guided three-step therapy for high grade glioma with Yttrium-90 biotin" Eur. J. Nucl. Med. 26:348-357 (1999).
Prashanta et al. "Tenascin in human neoplasia: Immunohistochemical observations using seven different clones of monoclonal antibodies" Intl. J. Oncol. 8:741-755 (1996).
Reznik et al, "Streptavidins with intersubunit crosslinks have enhanced stability" Nature Biotechnol. 14:1007-1011 (1998).
Rudikoff et al. "Single amino acid substitution altering antigen-binding specificity" Proc. Natl. Acad. Sci. USA 79:1979-1983 (1982).
International Search Report for PCT/IT2003/00098 dated Jul. 16, 2003.
International Preliminary Examination Report for PCT/IT2003/00098 dated Feb. 3, 2004.

* cited by examiner

*Primary Examiner* — Maher Haddad
(74) *Attorney, Agent, or Firm* — Lucas & Mercanti, LLP

(57) ABSTRACT

A novel anti-human tenascin ST2146 monoclonal antibody is described endowed with high affinity with the native antigen and high tumor selectivity. The cST2146 hybridoma is stably producing the antibody in high density culture conditions and is suitable for the industrial development of ST2146-based products. ST2146 exhibits properties exploitable for both therapeutic and diagnostic applications.

23 Claims, 11 Drawing Sheets

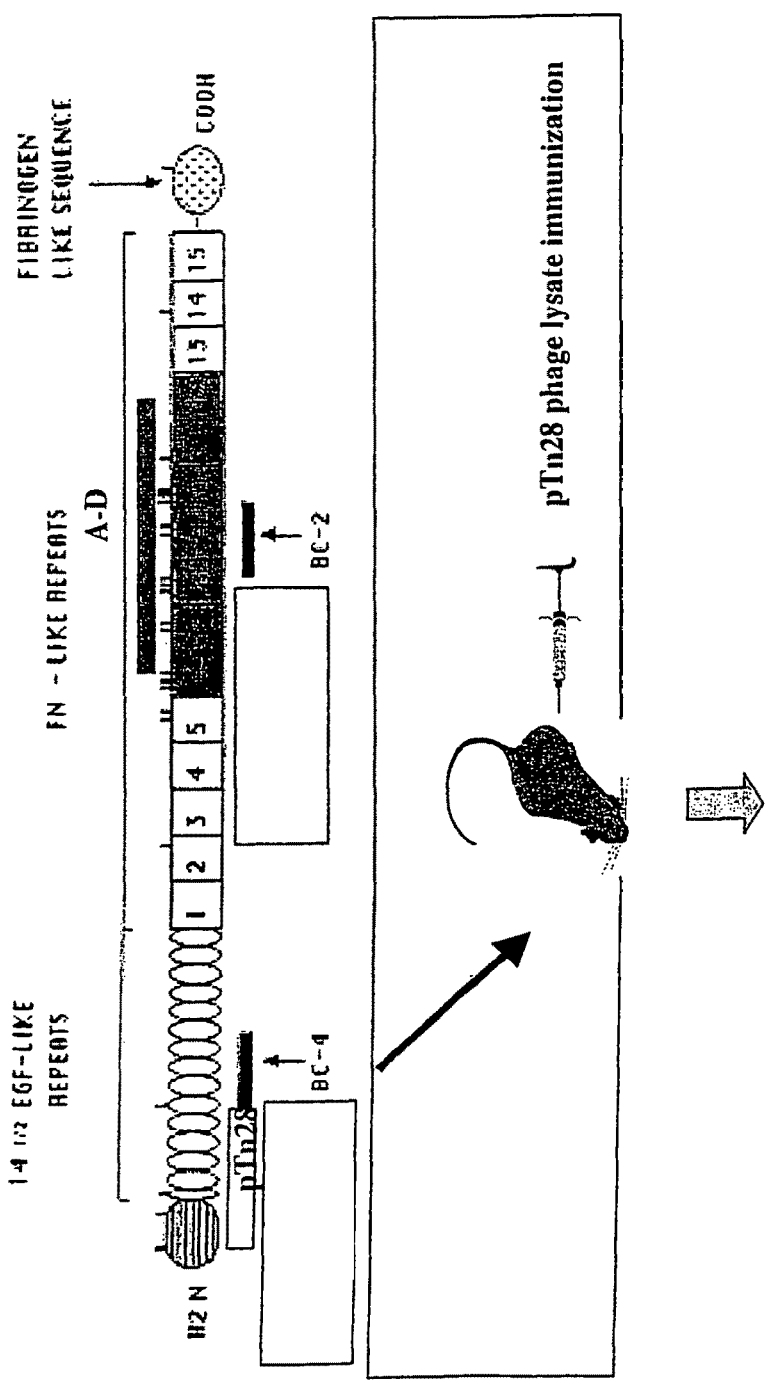
Figure 1: Schematic representation of human tenascin-C and strategy to generate BC4-like antibodies

Figure 2: Digestion of sialic residues on ST2146

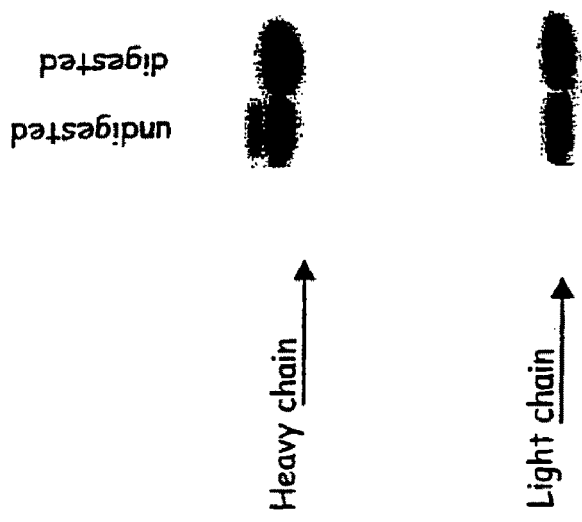

ST2146 was buffer exchanged with a HiTrap desalting column (Amersham-Pharmacia), to 10mM sodium phosphate buffer containing 150mM NaCl, pH6.4. The Mab was concentrated on centricons 100.000 MWCO (Millipore) to a final concentration of about 1mg/ml and digested with 1.5 U/ml of sialidase (Sigma) for 24 hrs at 37°C. The samples were subjected to electrophoresis on 12% polyacrylamide slab gel. Gel staining was done by Coomassie Brilliant Blue.

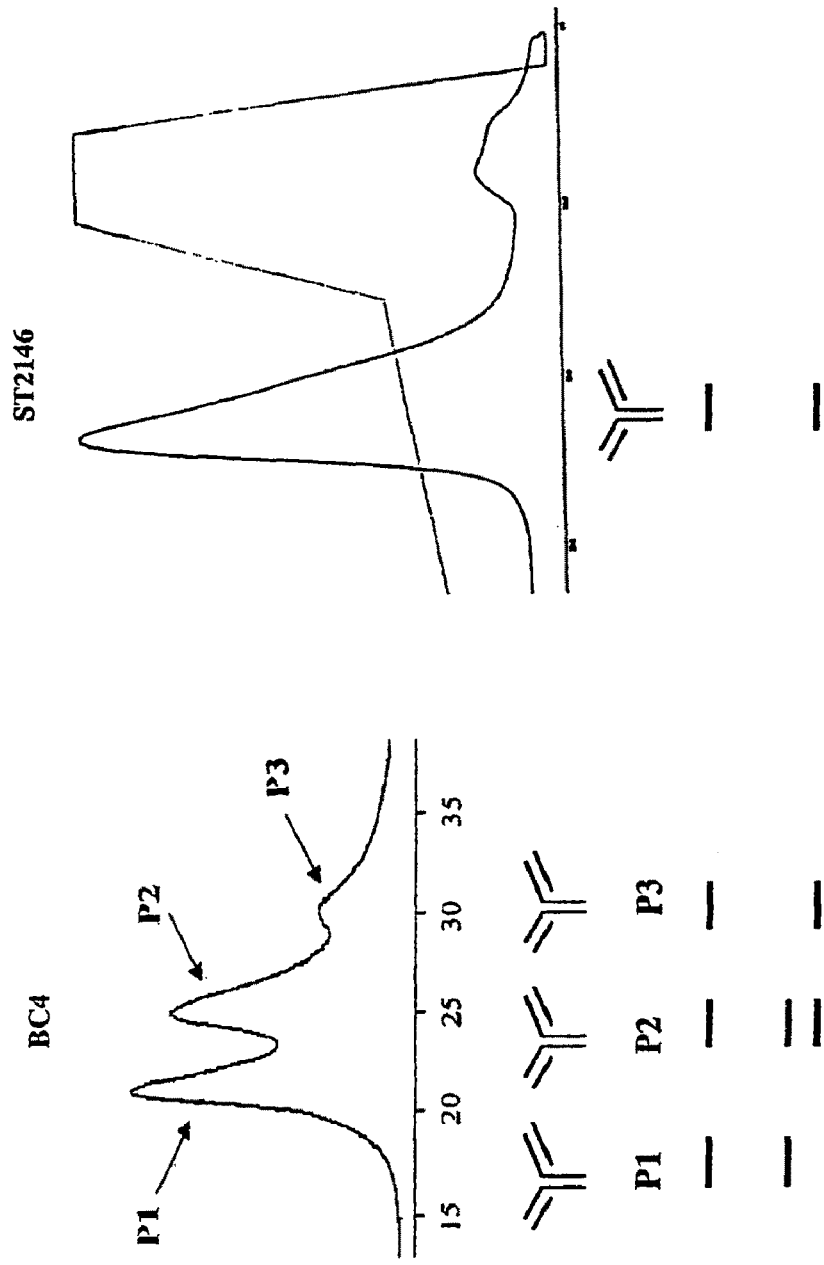
Figure 3: Hydroxylapatite chromatography of BC4 and ST2146 anti-tenascin Mabs
Note: The red light chain was found to be non functional. Therefore, fully functional BC4 corresponds only to peak 3.

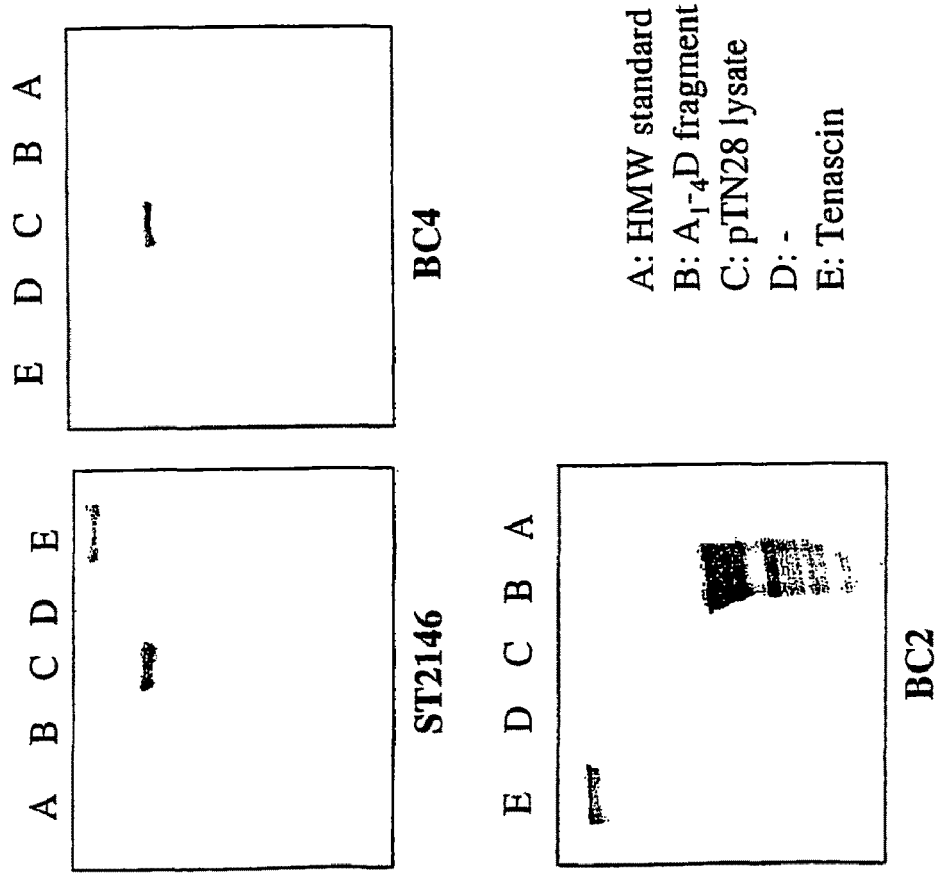
Figure 4: Western Blot analysis of anti-tenascin antibodies

Figure 5: ST2146 competitive ELISA

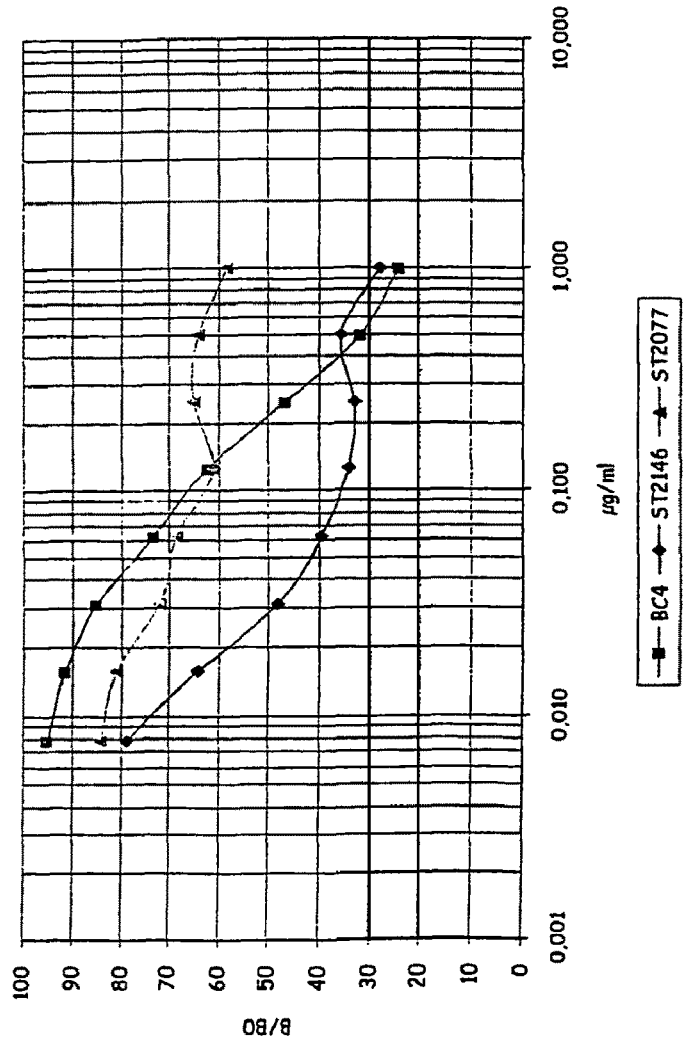

Biotinylated BC4 was mixed with increasing concentrations of BC4, ST2077 or ST2146 as competitors and plated on tenascin coated plates. Binding was measured after addition of HRP-streptavidin and related chromogenic substrate.
ST2077 is an antibody recognizing an epitope of tenascin within the EGF-like repeat, partially shared with the BC4 epitope.

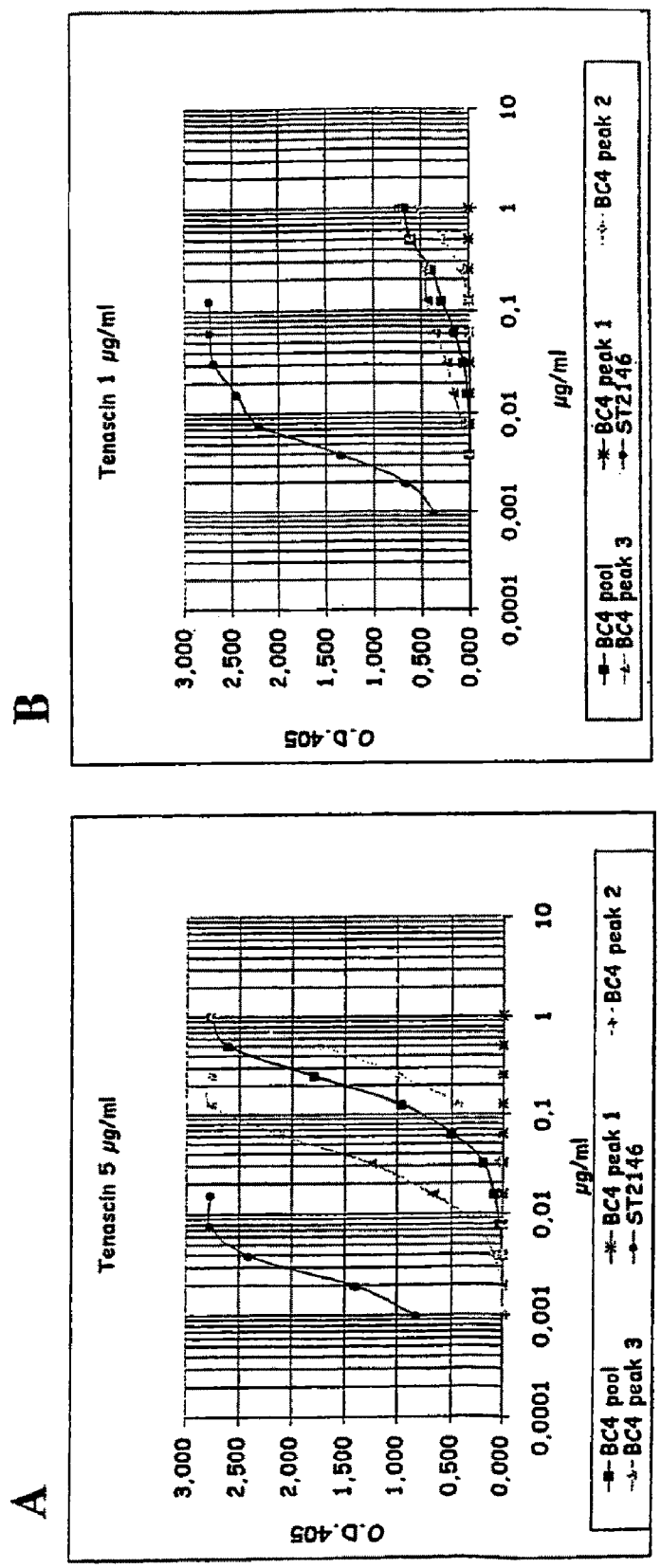
Figure 6: Immunoreactivity of ST2146 and BC4

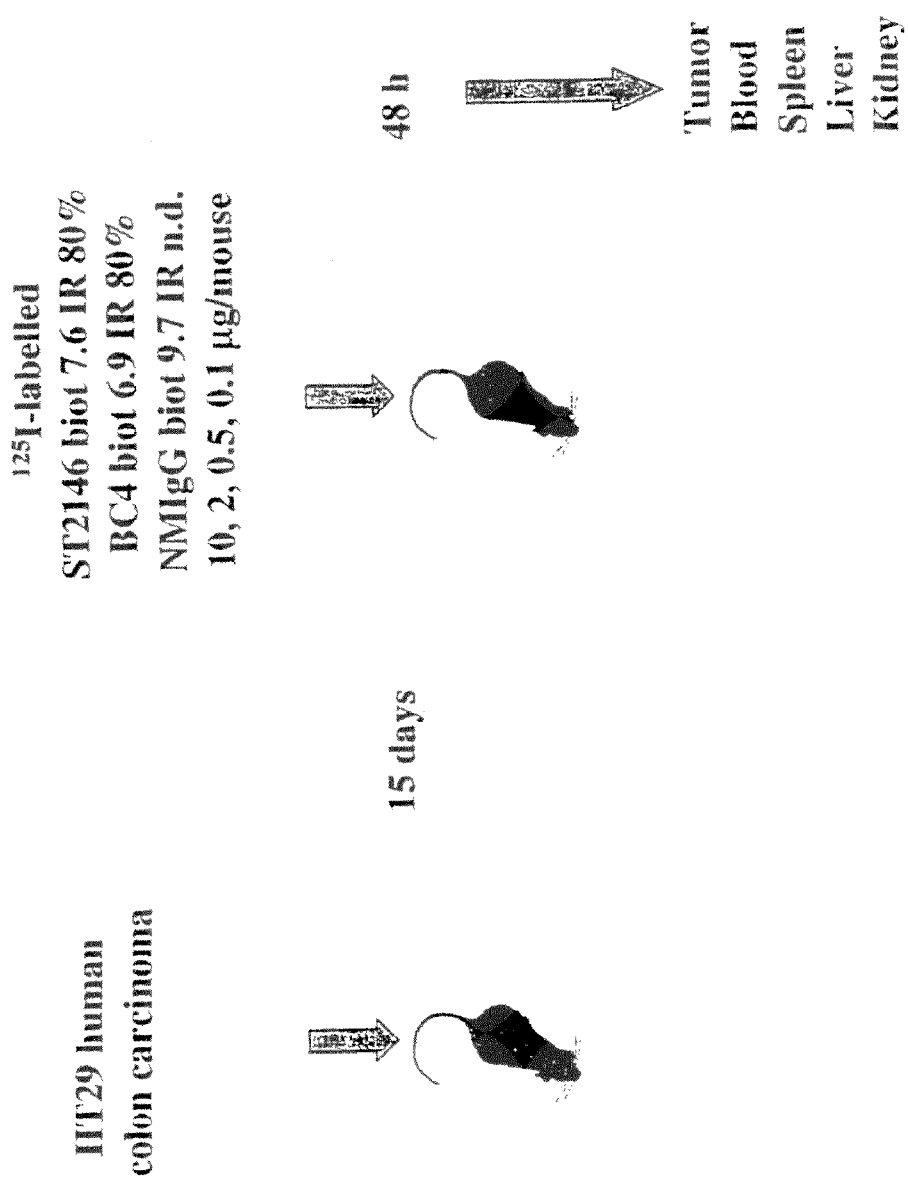

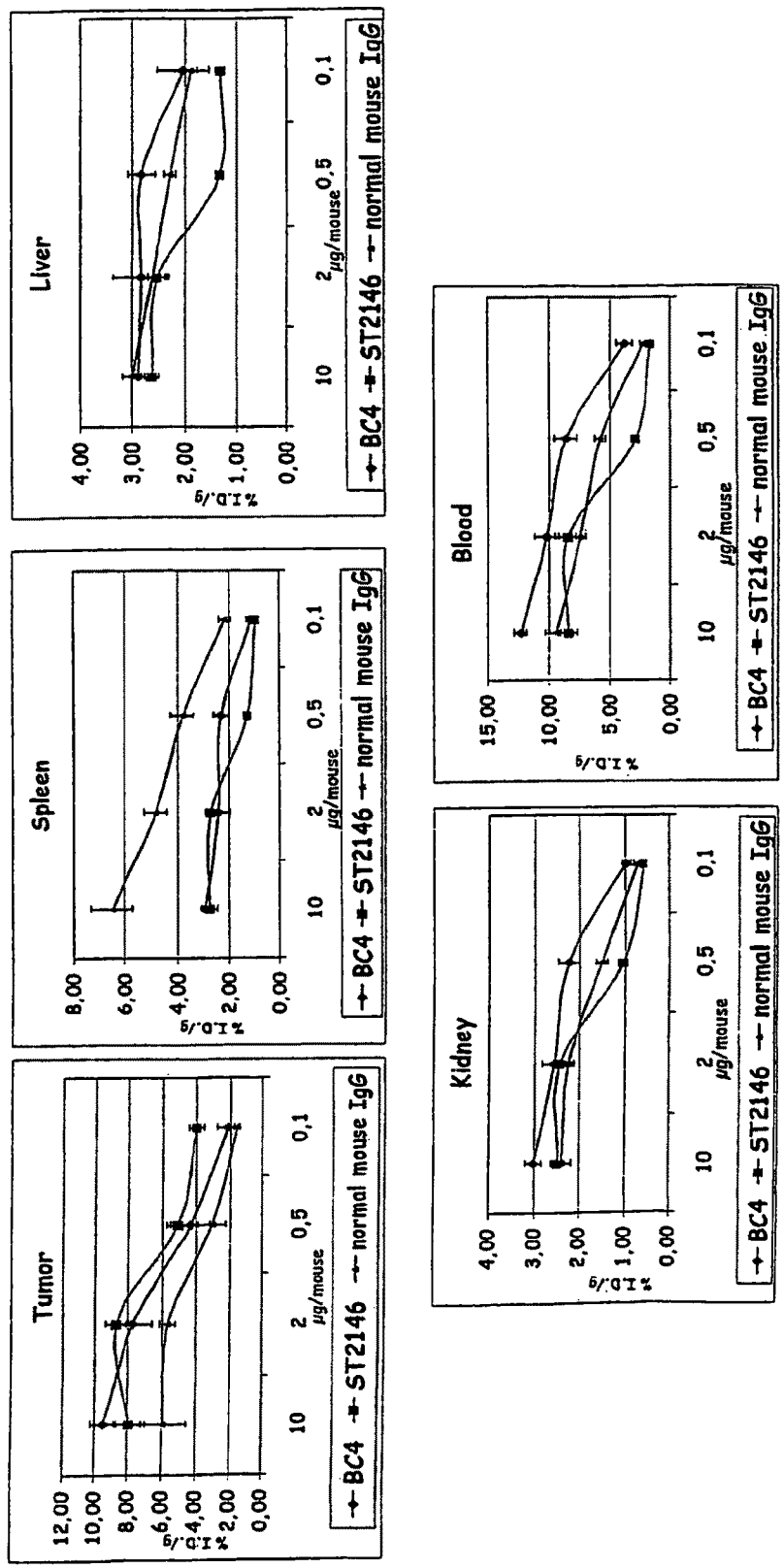
Figure 8: Biodistribution of ST2146 and BC4 biotinylated Mabs in tumor grafted nude mice

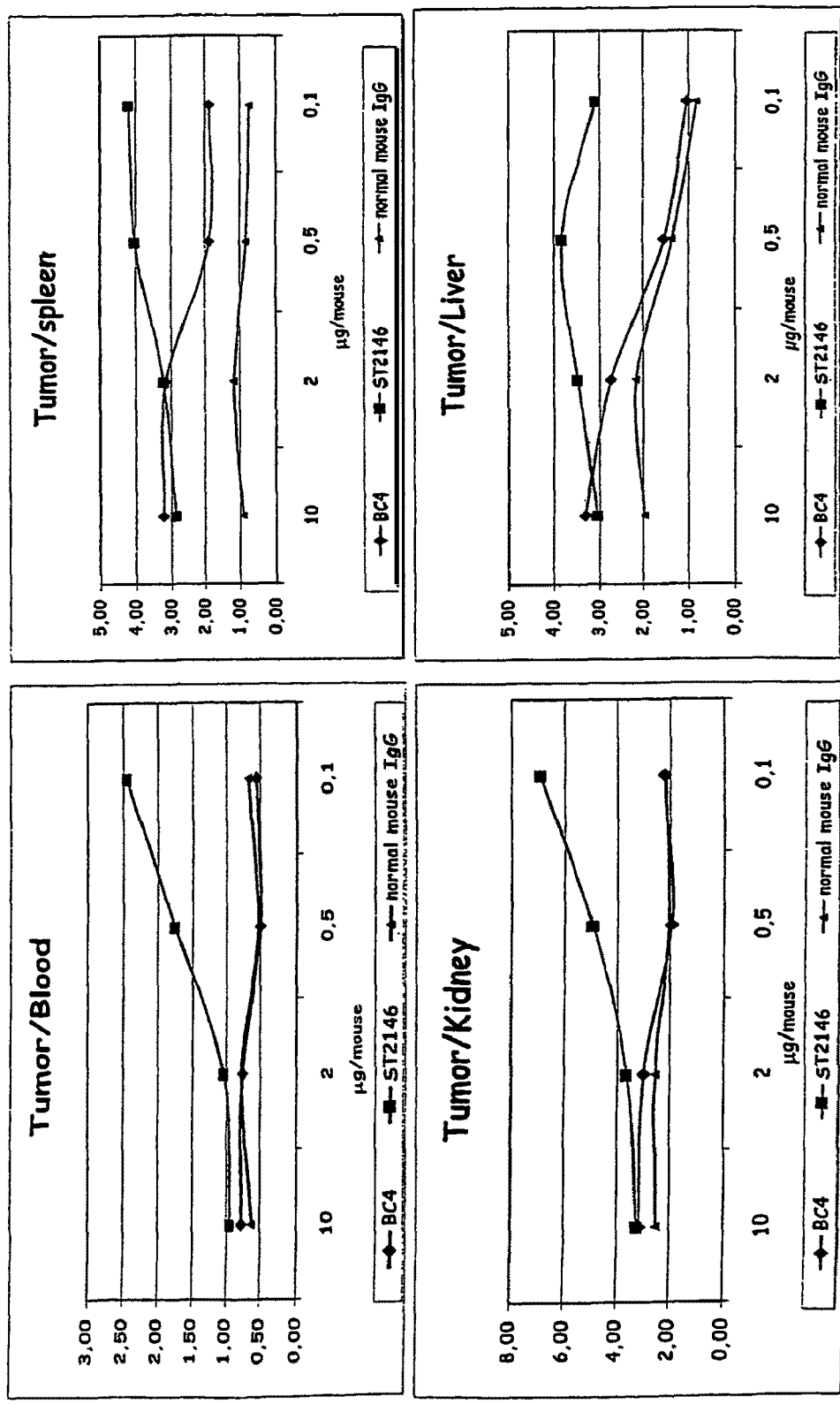
Figure 9: Tumor/Non Tumor Ratio of ST2146 and BC4 biotinylated Mabs in tumor grafted nude mice

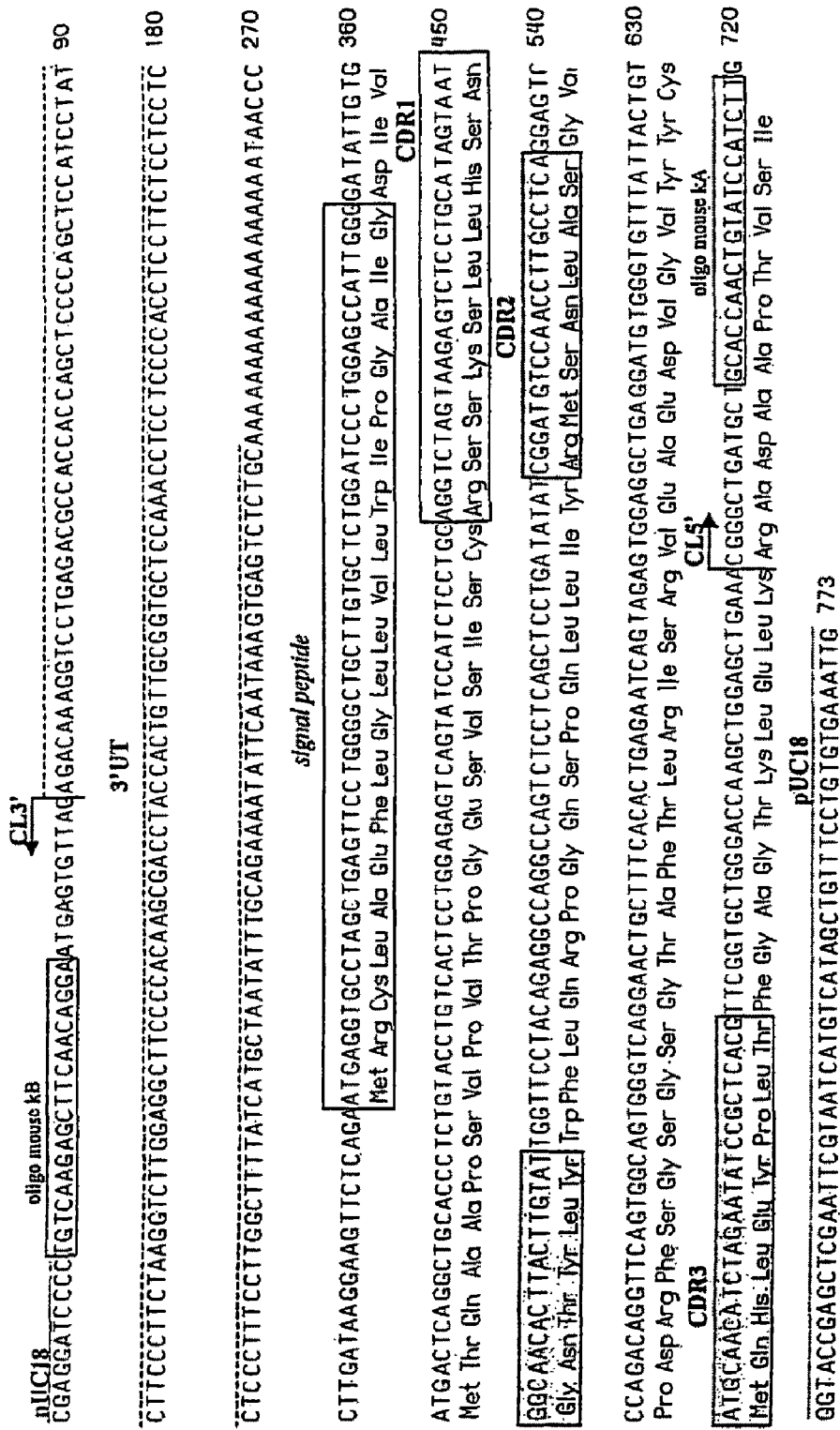
Figure 10: ST2146 light chain variable cDNA sequence and deduced aminoacid sequence
ST2146-D3d-F6e kappa light chain subgroup II

Figure 11: ST2146 heavy chain variable cDNA sequence and deduced aminoacid sequence oligo VH1 back

AGGTGAAACTGCAGGAGTCTGGACCTGAGCTGGTGAAGCCTGGGGCTTCAGTGAAGGTATCCTGCAAGGCTTCTGGTTATGCATTCACTA 90
Lys Val Lys Leu Gln Ser Gly Pro Glu Leu Val Lys Pro Gly Ala Ser Val Lys Val Ser Cys Lys Ala Ser Gly Tyr Ala Phe Thr

CDR1                                                                                            CDR2
GCTACAACATGTACTGGGTGAAGCAGAGCCATGGAAAGAGCCTTGAGTGGATTGGATATATTGATCCTTACAATGGTGTTACTAGCTACA 180
Ala Tyr Asn Met Tyr Trp Val Lys Gln Ser His Gly Lys Ser Leu Glu Trp Ile Gly Tyr Ile Asp Pro Tyr Asn Gly Val Thr Ser Tyr

ACCAGAAGTTCAAGGGCAAGGCCACATTGACTGTTGACAAGTCCTCCAGCACAGCCTACATGCATCTCAACAGCCTGACACTCTGAGGACT 270
Asn Gln Lys Phe Lys Gly Lys Ala Thr Leu Thr Val Asp Lys Ser Ser Ser Thr Ala Tyr Met His Leu Asn Ser Leu Thr Ser Glu Asp oligo VH1 for
CTGCAGTCTATTACTGTGCAAGAGGGGGCGGTAGTATCTACTATGGCTATGGACTAGTGGGGCCAAGGGACCACGGTCACCGTCTCCTCA 359
Ser Ala Val Tyr Tyr Cys Ala Arg Gly Gly Gly Ser Ile Tyr Tyr Ala Met Asp Tyr Trp Gly Gln Gly Thr Thr Val Thr Val Ser Ser

CDR3

ST2146 gamma heavy chain subgroup IIA

SEQUENCE LISTING

<160> NUMBER OF SEQ ID NOS: 22

<210> SEQ ID NO 1
<211> LENGTH: 142
<212> TYPE: PRT
<213> ORGANISM: Artificial Sequence
<220> FEATURE:
<223> OTHER INFORMATION: synthetic ST2146 light chain variable region
      protein sequence

<400> SEQUENCE: 1

Met Arg Cys Leu Ala Glu Phe Leu Gly Leu Leu Val Leu Trp Ile Pro
 1               5                  10                  15

Gly Ala Ile Gly Asp Ile Val Met Thr Gln Ala Ala Pro Ser Val Pro
                20                  25                  30

Val Thr Pro Gly Glu Ser Val Ser Ile Ser Cys Arg Ser Ser Lys Ser
            35                  40                  45

Leu Leu His Ser Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
 65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
        115                 120                 125

Leu Glu Leu Lys Arg Ala Asp Ala Ala Pro Thr Val Ser Ile
    130                 135                 140

<210> SEQ ID NO 2
<211> LENGTH: 120
<212> TYPE: PRT
<213> ORGANISM: Artificial Sequence
<220> FEATURE:
<223> OTHER INFORMATION: synthetic ST2146 heavy chain variable region
      protein sequence

<400> SEQUENCE: 2

Lys Val Lys Leu Gln Gln Ser Gly Pro Glu Leu Val Lys Pro Gly Ala
 1               5                  10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Val Thr Ser Tyr Asn Gln Lys Phe
        50                  55                  60

Lys Gly Lys Ala Thr Leu Thr Val Asp Lys Ser Ser Ser Thr Ala Tyr
 65                  70                  75                  80

```
            Met His Leu Asn Ser Leu Thr Ser Glu Asp Ser Ala Val Tyr Tyr Cys
                            85                  90                  95

Ala Arg Gly Gly Gly Ser Ile Tyr Tyr Ala Met Asp Tyr Trp Gly Gln
                        100                 105                 110

Gly Thr Thr Val Thr Val Ser Ser
                    115                 120
```

<210> SEQ ID NO 3
<211> LENGTH: 426
<212> TYPE: DNA
<213> ORGANISM: Artificial Sequence
<220> FEATURE:
<223> OTHER INFORMATION: synthetic ST2146 light chain variable region
      cDNA sequence
<220> FEATURE:
<221> NAME/KEY: CDS
<222> LOCATION: (1)..(426)

<400> SEQUENCE: 3

```
atg agg tgc cta gct gag ttc ctg ggg ctg ctt gtg ctc tgg atc cct        48
Met Arg Cys Leu Ala Glu Phe Leu Gly Leu Leu Val Leu Trp Ile Pro
 1               5                  10                  15 gga gcc att ggg gat att gtg atg act cag gct gca ccc tct gta cct        96
Gly Ala Ile Gly Asp Ile Val Met Thr Gln Ala Ala Pro Ser Val Pro
                20                  25                  30 gtc act cct gga gag tca gta tcc atc tcc tgc agg tct agt aag agt       144
Val Thr Pro Gly Glu Ser Val Ser Ile Ser Cys Arg Ser Ser Lys Ser
            35                  40                  45 ctc ctg cat agt aat ggc aac act tac ttg tat tgg ttc cta cag agg       192
Leu Leu His Ser Asn Gly Asn Thr Tyr Leu Tyr Trp Phe Leu Gln Arg
        50                  55                  60 cca ggc cag tct cct cag ctc ctg ata tat cgg atg tcc aac ctt gcc       240
Pro Gly Gln Ser Pro Gln Leu Leu Ile Tyr Arg Met Ser Asn Leu Ala
 65                  70                  75                  80 tca gga gtc cca gac agg ttc agt ggc agt ggg tca gga act gct ttc       288
Ser Gly Val Pro Asp Arg Phe Ser Gly Ser Gly Ser Gly Thr Ala Phe
                 85                  90                  95 aca ctg aga atc agt aga gtg gag gct gag gat gtg ggt gtt tat tac       336
Thr Leu Arg Ile Ser Arg Val Glu Ala Glu Asp Val Gly Val Tyr Tyr
            100                 105                 110 tgt atg caa cat cta gaa tat ccg ctc acg ttc ggt gct ggg acc aag       384
Cys Met Gln His Leu Glu Tyr Pro Leu Thr Phe Gly Ala Gly Thr Lys
        115                 120                 125 ctg gag ctg aaa cgg gct gat gct gca cca act gta tcc atc                426
Leu Glu Leu Lys Arg Ala Asp Ala Ala Pro Thr Val Ser Ile
130                 135                 140
```

<210> SEQ ID NO 4
<211> LENGTH: 360
<212> TYPE: DNA
<213> ORGANISM: Artificial Sequence
<220> FEATURE:
<223> OTHER INFORMATION: synthetic ST2146 heavy chain variable region
      cDNA sequence
<220> FEATURE:
<221> NAME/KEY: CDS
<222> LOCATION: (1)..(360)

<400> SEQUENCE: 4

```
aag gtg aaa ctg cag cag tct gga cct gag ctg gtg aag cct ggg gct        48
Lys Val Lys Leu Gln Gln Ser Gly Pro Glu Leu Val Lys Pro Gly Ala
 1               5                  10                  15 tca gtg aag gta tcc tgc aag gct tct ggt tat gca ttc act agc tac        96
Ser Val Lys Val Ser Cys Lys Ala Ser Gly Tyr Ala Phe Thr Ser Tyr
                20                  25                  30
```

-continued

```
aac atg tac tgg gtg aag cag agc cat gga aag agc ctt gag tgg att    144
Asn Met Tyr Trp Val Lys Gln Ser His Gly Lys Ser Leu Glu Trp Ile
         35                  40                  45 gga tat att gat cct tac aat ggt gtt act agc tac aac cag aag ttc    192
Gly Tyr Ile Asp Pro Tyr Asn Gly Val Thr Ser Tyr Asn Gln Lys Phe
 50                  55                  60 aag ggc aag gcc aca ttg act gtt gac aag tcc tcc agc aca gcc tac    240
Lys Gly Lys Ala Thr Leu Thr Val Asp Lys Ser Ser Ser Thr Ala Tyr
 65                  70                  75                  80 atg cat ctc aac agc ctg aca tct gag gac tct gca gtc tat tac tgt    288
Met His Leu Asn Ser Leu Thr Ser Glu Asp Ser Ala Val Tyr Tyr Cys
             85                  90                  95 gca aga ggg ggc ggt agt atc tac tat gct atg gac tac tgg ggc caa    336
Ala Arg Gly Gly Gly Ser Ile Tyr Tyr Ala Met Asp Tyr Trp Gly Gln
             100                 105                 110 ggg acc acg gtc acc gtc tcc tca                                    360
Gly Thr Thr Val Thr Val Ser Ser
         115                 120
```

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
tgtcaagagc ttcaacagga                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
aagatggata cagttggtgc                                              20

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
gtcactgact cagggaagta gcc                                          23

<210> SEQ ID NO 8
<211> LENGTH: 23
<212> TYPE: DNA
<213> ORGANISM: Artificial Sequence
<220> FEATURE:
<223> OTHER INFORMATION: synthetic primer

<400> SEQUENCE: 8
gcaacgtgag acacgagggt ctg                                          23

<210> SEQ ID NO 9
<211> LENGTH: 16
<212> TYPE: PRT
<213> ORGANISM: Artificial Sequence
<220> FEATURE:
<223> OTHER INFORMATION: synthetic ST2146 light chain variable region
      CDR1 peptide sequence

```
<400> SEQUENCE: 9

Arg Ser Ser Lys Ser Leu Leu His Ser Asn Gly Asn Thr Tyr Leu Tyr
 1               5                  10                  15

<210> SEQ ID NO 10
<211> LENGTH: 48
<212> TYPE: DNA
<213> ORGANISM: Artificial Sequence
<220> FEATURE:
<223> OTHER INFORMATION: synthetic ST2146 light chain variable region
      CDR1 nucleotide sequence
<220> FEATURE:
<221> NAME/KEY: CDS
<222> LOCATION: (1)..(48)

<400> SEQUENCE: 10 agg tct agt aag agt ctc ctg cat agt aat ggc aac act tac ttg tat      48
Arg Ser Ser Lys Ser Leu Leu His Ser Asn Gly Asn Thr Tyr Leu Tyr
 1               5                  10                  15

<210> SEQ ID NO 11
<211> LENGTH: 7
<212> TYPE: PRT
<213> ORGANISM: Artificial Sequence
<220> FEATURE:
<223> OTHER INFORMATION: synthetic ST2146 light chain variable region
      CDR2 peptide sequence

<400> SEQUENCE: 11

Arg Met Ser Asn Leu Ala Ser
 1               5

<210> SEQ ID NO 12
<211> LENGTH: 21
<212> TYPE: DNA
<213> ORGANISM: Artificial Sequence
<220> FEATURE:
<223> OTHER INFORMATION: synthetic ST2146 light chain variable region
      CDR2 nucleotide sequence
<220> FEATURE:
<221> NAME/KEY: CDS
<222> LOCATION: (1)..(21)

<400> SEQUENCE: 12 cgg atg tcc aac ctt gcc tca                                          21
Arg Met Ser Asn Leu Ala Ser
 1               5

<210> SEQ ID NO 13
<211> LENGTH: 9
<212> TYPE: PRT
<213> ORGANISM: Artificial Sequence
<220> FEATURE:
<223> OTHER INFORMATION: synthetic ST2146 light chain variable region
      CDR3 peptide sequence

<400> SEQUENCE: 13

Met Gln His Leu Glu Tyr Pro Leu Thr
 1               5

<210> SEQ ID NO 14
<211> LENGTH: 27
<212> TYPE: DNA
<213> ORGANISM: Artificial Sequence
<220> FEATURE:
<223> OTHER INFORMATION: synthetic ST2146 light chain variable region
      CDR3 nucleotide sequence
<220> FEATURE:
<221> NAME/KEY: CDS
<222> LOCATION: (1)..(27)
```

-continued

```
<400> SEQUENCE: 14 atg caa cat cta gaa tat ccg ctc acg                              27
Met Gln His Leu Glu Tyr Pro Leu Thr
 1               5

<210> SEQ ID NO 15
<211> LENGTH: 5
<212> TYPE: PRT
<213> ORGANISM: Artificial Sequence
<220> FEATURE:
<223> OTHER INFORMATION: synthetic ST2146 heavy chain variable region
      CDR1 peptide sequence

<400> SEQUENCE: 15

Ser Tyr Asn Met Tyr
 1               5

<210> SEQ ID NO 16
<211> LENGTH: 15
<212> TYPE: DNA
<213> ORGANISM: Artificial Sequence
<220> FEATURE:
<223> OTHER INFORMATION: synthetic ST2146 heavy chain variable region
      CDR1 nucleotide sequence
<220> FEATURE:
<221> NAME/KEY: CDS
<222> LOCATION: (1)..(15)

<400> SEQUENCE: 16 agc tac aac atg tac                                              15
Ser Tyr Asn Met Tyr
 1               5

<210> SEQ ID NO 17
<211> LENGTH: 17
<212> TYPE: PRT
<213> ORGANISM: Artificial Sequence
<220> FEATURE:
<223> OTHER INFORMATION: synthetic ST2146 heavy chain variable region
      CDR2 peptide sequence

<400> SEQUENCE: 17

Tyr Ile Asp Pro Tyr Asn Gly Val Thr Ser Tyr Asn Gln Lys Phe Lys
 1               5                  10                  15

Gly

<210> SEQ ID NO 18
<211> LENGTH: 51
<212> TYPE: DNA
<213> ORGANISM: Artificial Sequence
<220> FEATURE:
<223> OTHER INFORMATION: synthetic ST2146 heavy chain variable region
      CDR2 nucleotide sequence
<220> FEATURE:
<221> NAME/KEY: CDS
<222> LOCATION: (1)..(51)

<400> SEQUENCE: 18 tat att gat cct tac aat ggt gtt act agc tac aac cag aag ttc aag  48
Tyr Ile Asp Pro Tyr Asn Gly Val Thr Ser Tyr Asn Gln Lys Phe Lys
 1               5                  10                  15 ggc                                                              51
Gly

<210> SEQ ID NO 19
<211> LENGTH: 11
<212> TYPE: PRT
<213> ORGANISM: Artificial Sequence
```

```
<220> FEATURE:
<223> OTHER INFORMATION: synthetic ST2146 heavy chain variable region
      CDR3 peptide sequence

<400> SEQUENCE: 19

Gly Gly Gly Ser Ile Tyr Tyr Ala Met Asp Tyr
 1               5                  10

<210> SEQ ID NO 20
<211> LENGTH: 33
<212> TYPE: DNA
<213> ORGANISM: Artificial Sequence
<220> FEATURE:
<223> OTHER INFORMATION: synthetic ST2146 heavy chain variable region
      CDR3 nucleotide sequence
<220> FEATURE:
<221> NAME/KEY: CDS
<222> LOCATION: (1)..(33)

<400> SEQUENCE: 20 ggg ggc ggt agt atc tac tat gct atg gac tac                         33
Gly Gly Gly Ser Ile Tyr Tyr Ala Met Asp Tyr
 1               5                  10

<210> SEQ ID NO 21
<211> LENGTH: 773
<212> TYPE: DNA
<213> ORGANISM: Artificial Sequence
<220> FEATURE:
<223> OTHER INFORMATION: synthetic ST2146 light chain variable region
      nucleotide sequence
<220> FEATURE:
<221> NAME/KEY: CDS
<222> LOCATION: (292)..(717)

<400> SEQUENCE: 21
cgaggatccc ctgtcaagag cttcaacagg aatgagtgtt agagacaaag gtcctgagac     60
gccaccacca gctccccagc tccatcctat cttcccttct aaggtcttgg aggcttcccc    120
acaagcgacc taccactgtt gcggtgctcc aaacctcctc cccacctcct tctcctcctc    180 ctcccttttcc ttggcttttta tcatgctaat atttgcagaa atattcaat aaagtgagtc    240 tctgcaaaaa aaaaaaaaaa aaaataaccc cttgataagg aagttctcag a atg agg     297
                                                         Met Arg
                                                           1 tgc cta gct gag ttc ctg ggg ctg ctt gtg ctc tgg atc cct gga gcc     345
Cys Leu Ala Glu Phe Leu Gly Leu Leu Val Leu Trp Ile Pro Gly Ala
        5                  10                  15 att ggg gat att gtg atg act cag gct gca ccc tct gta cct gtc act     393
Ile Gly Asp Ile Val Met Thr Gln Ala Ala Pro Ser Val Pro Val Thr
 20                  25                  30 cct gga gag tca gta tcc atc tcc tgc agg tct agt aag agt ctc ctg     441
Pro Gly Glu Ser Val Ser Ile Ser Cys Arg Ser Ser Lys Ser Leu Leu
 35                  40                  45                  50 cat agt aat ggc aac act tac ttg tat tgg ttc cta cag agg cca ggc     489
His Ser Asn Gly Asn Thr Tyr Leu Tyr Trp Phe Leu Gln Arg Pro Gly
                 55                  60                  65 cag tct cct cag ctc ctg ata tat cgg atg tcc aac ctt gcc tca gga     537
Gln Ser Pro Gln Leu Leu Ile Tyr Arg Met Ser Asn Leu Ala Ser Gly
         70                  75                  80 gtc cca gac agg ttc agt ggc agt ggg tca gga act gct ttc aca ctg     585
Val Pro Asp Arg Phe Ser Gly Ser Gly Ser Gly Thr Ala Phe Thr Leu
     85                  90                  95 aga atc agt aga gtg gag gct gag gat gtg ggt gtt tat tac tgt atg     633
Arg Ile Ser Arg Val Glu Ala Glu Asp Val Gly Val Tyr Tyr Cys Met
100                 105                 110
```

```
caa cat cta gaa tat ccg ctc acg ttc ggt gct ggg acc aag ctg gag        681
Gln His Leu Glu Tyr Pro Leu Thr Phe Gly Ala Gly Thr Lys Leu Glu
115                 120                 125                 130 ctg aaa cgg gct gat gct gca cca act gta tcc atc ttgggtaccg             727
Leu Lys Arg Ala Asp Ala Ala Pro Thr Val Ser Ile
                135                 140 agctcgaatt cgtaatcatg tcatagctgt ttcctgtgtg aaattg                     773

<210> SEQ ID NO 22
<211> LENGTH: 360
<212> TYPE: DNA
<213> ORGANISM: Artificial Sequence
<220> FEATURE:
<223> OTHER INFORMATION: synthetic ST2146 heavy chain variable region
      nucleotide sequence
<220> FEATURE:
<221> NAME/KEY: CDS
<222> LOCATION: (1)..(360)

<400> SEQUENCE: 22 aag gtg aaa ctg cag cag tct gga cct gag ctg gtg aag cct ggg gct         48
Lys Val Lys Leu Gln Gln Ser Gly Pro Glu Leu Val Lys Pro Gly Ala
1               5                   10                  15 tca gtg aag gta tcc tgc aag gct tct ggt tat gca ttc act agc tac         96
Ser Val Lys Val Ser Cys Lys Ala Ser Gly Tyr Ala Phe Thr Ser Tyr
                20                  25                  30 aac atg tac tgg gtg aag cag agc cat gga aag agc ctt gag tgg att        144
Asn Met Tyr Trp Val Lys Gln Ser His Gly Lys Ser Leu Glu Trp Ile
            35                  40                  45 gga tat att gat cct tac aat ggt gtt act agc tac aac cag aag ttc        192
Gly Tyr Ile Asp Pro Tyr Asn Gly Val Thr Ser Tyr Asn Gln Lys Phe
        50                  55                  60 aag ggc aag gcc aca ttg act gtt gac aag tcc tcc agc aca gcc tac        240
Lys Gly Lys Ala Thr Leu Thr Val Asp Lys Ser Ser Ser Thr Ala Tyr
65                  70                  75                  80 atg cat ctc aac agc ctg aca tct gag gac tct gca gtc tat tac tgt        288
Met His Leu Asn Ser Leu Thr Ser Glu Asp Ser Ala Val Tyr Tyr Cys
                85                  90                  95 gca aga ggg ggt ggt agt atc tac tat gct atg gac tac tgg ggc caa        336
Ala Arg Gly Gly Gly Ser Ile Tyr Tyr Ala Met Asp Tyr Trp Gly Gln
            100                 105                 110 ggg acc acg gtc acc gtc tcc tca                                        360
Gly Thr Thr Val Thr Val Ser Ser
        115                 120
```

ANTI-HUMAN TENASCIN MONOCLONAL ANTIBODY

This application is a continuation of Application No. 10/505,747, filed Aug. 25, 2004, now U.S. Pat. No. 7,438,908; which is a continuation under 35 U.S.C. 371 of Int'l Application No. PCT/IT2003/00098 filed Feb. 20, 2003; which claims the benefit of provisional Application No. 60/359,299, filed Feb. 26, 2002. The entire contents of each of which are hereby incorporated by reference in this application.

The present invention relates to monoclonal antibodies anti-human tenascin, methods and materials for obtaining them, the use of said antibodies for the preparation of diagnostic means and medicaments for the diagnosis and treatment, respectively, of tumors expressing tenascin and materials comprising said antibodies suitable for use in medical field.

BACKGROUND OF THE INVENTION

The specificity of tumor therapy is often a limiting step in determining the success of a treatment. In fact, the onset of toxic effects and the reduced tolerability of certain anticancer agents limit their use and the quality of life of patients.

The reduction of toxicity is directly linked to the selectivity of the treatment for cancer cells. Monoclonal antibodies represent the ideal means for the specific targeting of tumors and, when combined with the avidin/biotin amplification system, constitute an extremely powerful and selective way to deliver active moieties at the tumor site.

Tenascin is one of the extracellular matrix proteins and shows site-restricted expression during embryogenesis and can be found in adult tissues during wound healing and tumorigenesis, as well as in newly formed tumor blood vessels. Tenascin is absent in normal adult tissue, but is expressed in the stroma of a variety of solid tumors, such as gliomas (Burdon, et al., *Cancer Res.* 43:2796-2805, 1983), mammary (Chiquet-Ehrisinann, et al., 1986), lung carcinomas (Natali et al., *Intl. J. Cancer* 54:56-68, 1989), fibrosarcomas and squamous cell carcinomas (Ramos D. M. et al., *Int. J. Cancer* 75:680-687, 1998). Tenascin is found in gliomas, but not in normal brain tissue. For a discussion on tenascin, reference can be made to WO 92/04464, Wistar, and the related references.

Based on the teaching of EP 0 496 074, G. Paganelli et al developed a three-step pre-targeting approach for the systemic and locoregional treatment of tumors (Cremonesi M et al., *Eur. J. Nucl. Med.* 26(2):110-120, 1999; Paganelli G. et al., *Eur. J. Nucl. Med.* 26(4):348-357, 1999; Paganelli G., et al. *Cancer Biother. & Radiopharm.* 16(3):227-235, 2001).

Other references on the three-step pre-targeting method are WO 94/04702 and U.S. Pat. No. 5,578,287.

The three step pre-targeting treatment is based on intravenous, sequential administration of a biotinylated anti-tenascin monoclonal antibody, streptavidin, and $^{90}$Y-labelled biotin with two chasing administrations of avidin and biotinylated albumin before streptavidin and $^{90}$Y-labelled biotin, respectively, to reduce non specific background. The selectivity of Paganelli's three step pre-targeting approach relies on the use of an anti-tenascin monoclonal antibody. Targeting of extra cellular matrix, compared to targeting of tumor cell antigens, exhibits the advantage of being unaffected by antigen modulation of tumor cells thus representing an ideal target for anti-tumor therapy.

The doses and timing of administrations of the three step pre-targeting treatment have been fixed in order to achieve optimal tumor/non tumor distribution ratio. Data obtained from 48 glioblastoma (GBM) or anaplastic astrocytoma (AA) patients, included in Paganelli's study, showed a substantial lack of toxicity, with the exception of some allergic reaction to streptavidin (which can be overcome by using avidin), and preliminary indication of therapeutic efficacy. In fact, 2 months after the end of treatment, 25% of patients showed a reduction in tumor size (Complete Response (Tumor reduction >50%)=6%; Partial Response (Tumor reduction <50%)= 11%; Minor Response (Tumor reduction <25%)=8%) and 52% of patients had not progressed, with an overall response rate of over 77%. In some of these patients, whose life expectancy was less than six months, the response persisted for more than a year (Paganelli et al., 1999).

The role of biotinylated anti-tenascin antibody is to localize at the tumor site and display biotins to mediate subsequent avidin and $^{90}$-Y-biotin accumulation.

Anti-tenascin antibodies are disclosed, for example, in U.S. Pat. No. 5,624,659, Duke University, JP 2219590, Rikagaku and the above mentioned WO 92/04464.

An anti-tenascin antibody is disclosed in Siri A. et al., *Nucl. Acid Res.* 19(3):525-531, 1991; Balza E. et al., *FEBS* 332:39-43, 1993 and its use for therapeutic purposes is disclosed in the above mentioned Cremonesi M. et al., *Eur. J. Nucl. Med.* 26(2):110-120, 1999; Paganelli G. et al., *Eur. J. Nucl. Med.* 26(4):348-357, 1999; Paganelli G. et al., *Cancer Biother. & Radiopharm.* 16(3):227-235, 2001. The clone used for generating the anti-tenascin antibody in the art is known as BC4.

The present applicant found the BC4 clone unsuitable for industrial development and regulatory purposes due to the production of an additional, non functional light chain (most likely of parental myeloma origin) whose level of expression increased under the pressure of scaling up cultivation, thus preventing large scale antibody purification.

SUMMARY OF THE INVENTION

It has now been found that an anti-human tenascin monoclonal antibody which solves the above mentioned problems, namely a monoclonal antibody lacking the expression of non functional light chains can be produced.

Therefore, this antibody is an object of the present invention, together with a method for obtaining said antibody, its use in therapy, in particular for the preparation of a medicament useful for the treatment of diseases characterized by the expression of tenascin, such as tumors.

DESCRIPTION OF THE INVENTION

The present invention provides an antibody and antibody fragments which may also contain additional markers and diagnostic agents, compositions containing these antibodies and antibody fragments, and diagnostic and therapeutic compositions containing them, their use in therapy and diagnostics and methods of making these antibody and antibody fragments.

The present invention is also directed to DNA encoding antibody and fragments, vectors containing DNA, host cells containing vectors, protein coded for by DNA encoding protein of SEQ ID NOs: 1 and 2; DNA encoding protein and fragments; specific CDRs and proteins comprising or containing CDRs According to the present invention, said antibody is, in one embodiment, characterised in that the light and heavy chain variable region sequences are SEQ ID NO:1 and SEQ ID NO:2, respectively. These sequences are shown in FIGS. 10 and 11. For sake of brevity, the preferred antibody according to the present invention shall be identified with the name ST2146. While the present invention focuses on ST2146, as an exemplification of the present invention, one of ordinary skill in the art will appreciate that, once given the present disclosure, other similar antibodies, and antibody fragments of ST 2146, as well as antibody fragments of these similar antibodies may be produced and used within the scope of the present invention. Such similar antibodies may be produced by a reasonable amount of experimentation by those skilled in the art.

The present invention therefore provides an antibody or antibody fragment or antibody chimera (such as, for example, a mouse-human chimera) or immunoglobulin molecule which specifically binds tenascin. The present invention provides an antibody or antibody fragment or antibody chimera or immunoglobulin molecule comprising at least one of a CDR of the variable light chain of ST2146 and/or a CDR of the variable heavy chain of ST2146. The antibody or antibody fragment or antibody chimera or immunoglobulin molecule of the present invention may be an antibody, an Fv fragment, an Fab fragment, a F(ab)$_2$ fragment, a single chain antibody, or a multimeric antibody. The antibody or antibody fragment or antibody chimera or immunoglobulin molecule of the present invention may be an IgM, IgD, IgG, IgA, or IgE molecule.

The present invention provides an antibody or antibody fragment or antibody chimera or immunoglobulin molecule comprising at least one of SEQ ID NOs: 1, 2, 9, 11, 13, 15, 17, or 19.

The present invention further provides nucleic acid sequences which encode the amino acid sequences of the present invention, such as the sequences of SEQ ID NOs: 1, 2, 9, 11, 13, 15, 17, or 19. The present invention provides therefore a DNA sequence encoding an antibody or antibody fragment or antibody chimera or immunoglobulin molecule of the present invention. Such DNA sequences include at least one DNA sequence or subsequence selected from SEQ ID NOs: 3, 4, 10, 21, 14, 16, 18 or 20.

Another embodiment is directed to a purified nucleic acid molecule encoding the antibody or antibody fragment or antibody chimera or immunoglobulin molecule product of the invention. A nucleic acid molecule encoding an immunoglobulin product of the invention may be made using conventional techniques. For example, oligonucleotides may be synthesized using oligonucleotide synthesizers and ligated together to form a functional open reading frame that encodes an immunoglobulin product of the invention. The nucleic acid molecule, once synthesized, may be cloned into a nucleic acid vector. A nucleic acid vector such as a plasmid, cosmid, phagemid, yeast plasmid, phage vectors, TI plasmid and the like are known in the art. The vector may be an expression vector. Expression vectors and expression systems are available commercially from supplies such as Stratagene (La Jolla, Calif.).

Another embodiment of the invention is directed to a cell comprising a nucleic acid of the invention. A cell may be made by transfection. Methods of transfection are known and kits for transfection of prokaryotic and eukaryotic cells may be purchased from commercial sources (e.g., Stratagene, La Jolla, Calif.)

Another embodiment of the invention is directed to a the use of the antibody, antibody fragment, antibody chimera or immunoglobulin product of the invention for means useful for detecting or diagnosing a disorder comprising the steps of contacting a tissue sample from a subject with under condition that permits the formation of a complex between said antibody, antibody fragment, antibody chimera or immunoglobulin product and a tenascin antigen, and determining the formation of said complex.

Another embodiment of the invention is directed to the use of an antibody, antibody fragment, antibody chimera or immunoglobulin product of the invention or a nucleic acid of the invention for the preparation of a medicament for the treatment of diseases expressing tenascin, in particular tumors. Methods for immunotherapy for cancer are known. See for example in Old, L. J. Immunotherapy for Cancer, Scientific American, September 1996.

Another embodiment is directed to a therapeutic composition comprising an antibody, antibody fragment, antibody chimera or immunoglobulin product of the invention. The immunoglobulin products of the invention may be provided in the form of a composition comprising the antibody, antibody fragment, antibody chimera or immunoglobulin product and a pharmaceutically acceptable carrier or diluent. The therapeutic composition may be used for the treatment of disorders in a mammal such as a human. The medicament shall be administered to a mammal in a therapeutically effective amount of the antibody, antibody fragment, antibody chimera or immunoglobulin product of the invention to the mammal.

In its use as a therapeutic agent, the antibody, antibody fragment, antibody chimera or immunoglobulin product of the invention may be linked to an agent. Linkage may be by covalent bonds or by antibody-epitope bond. For example, an antibody, antibody fragment, antibody chimera or immunoglobulin product may be crosslinked to a second antibody wherein the second antibody may have an affinity for the agent. The agent may be a cytotoxic agent. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof. The agent may be a chemotherapeutic agent. A chemotherapeutic agent is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, Vinorelbine, Carboplatin, Teniposide, Daunomycin, Caminomycin, Aminopterin, Dactinomycin, Mitomycins, Esperamicins (see U.S. Pat. No. 4,675,187), Melphalan and other related nitrogen mustards. The agent may be a cytokine. The term cytokine is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon-.alpha., -.beta., and -.gamma., colony stimulating factors (CSFs); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL9, IL-11, IL-12; a tumor necrosis factor; and other polypeptide factors including LIF and kit ligand (KL). As used herein, the term cytokine includes proteins from natural sources or from recombinant cell culture and biologically active equivalents of the native sequence cytokines.

For diagnosis, the antibody, antibody fragment, antibody chimera or immunoglobulin product of the invention may be attached to a label, such as to a detectable compound or composition which is conjugated directly or indirectly to the antibody. The label may be detectable by itself (e.g. radioisotope labels or fluorescent labels) or, in the case of an enzymatic label, may catalyze chemical alteration of a substrate compound or composition which is detectable.

The invention also contemplated the generation of mutants of the disclosed CDRs by the mutating, one or more amino acids in the sequence of the CDRs. It is known that a single amino acid substitution appropriately positioned in a CDR can be sufficient to raise the affinity Researcher have used site directed mutagenesis to increase affinity of some immunoglobulin products by about 10 fold. This method of increasing or decreasing affinity of antibodies by mutating CDRs is common knowledge (see, e.g., Chapter 23, Paul, W. E., Fundamental Immunology, Raven Press, NY, N.Y. 1993). Thus, the substitution, deletion, or addition of amino acids to the CDRs of the invention to increase or decrease binding affinity or specificity is also within the contemplation of this invention.

A further aspect of the present invention is providing a medicament for treating an individual with a tumour, such as a cystic brain tumours, gliomas, mammary tumours, lung carcinomas, fibrosarcomas or squamous cell carcinomas, which involves administering to a human subject afflicted with the tumour as a cystic brain tumor (e.g., one which expresses tenascin) an antibody, antibody fragment, antibody chimera or immunoglobulin product of the present invention that binds to tenascin in a therapeutically effective amount. The administering step may be carried out by depositing the antibody in the cavity of the tumor.

Also disclosed herein is a method of treating a solid tumor which comprises, first, removing a solid tumor (e.g., one which expresses tenascin) from a solid tissue organ (e.g., the brain) of an afflicted human subject; then forming an enclosed resection cavity in the organ of the subject at the location from which the solid tumor was removed; and then administering to the subject an antineoplastic agent such as an antibody, antibody fragment, antibody chimera or immunoglobulin product of the present invention (e.g., an antibody that binds to tenascin) which is selectively toxic to the cells of the solid tumor in a therapeutically effective amount. In an embodiment of the invention, the administering step is carried out by depositing the antineoplastic agent in the resection cavity.

Another object of the present invention are proteolytic fragments of said antibody, binding to an antigenic epitope within the EGF-like repeat of human tenascin C. In the course of the description of the present invention, for antibody fragments are intended those fragments which bind to an antigenic epitope within the EGF-like repeat of human tenascin C.

In another embodiment of the present invention, the antibody and the fragments thereof can further contain additional markers and/or diagnostic agents. Said markers and/or diagnostic agents are well-known to the person skilled in the art which the present invention is directed to.

According to a preferred embodiment of the present invention, said antibody or proteolytic fragments thereof are biotinylated.

Another object of the present invention is the hybridoma cell line, herein named cST2146, producing said antibody.

The hybridoma cell line has been deposited with Advanced Biotechnology Center, L.go Rosanna Benzi, 10 16132 GENOVA-Italy, on 29 Jan. 2002 under the provision of Budapest Treaty, and has been assigned Accession N°PD02003.

The present invention also comprises DNA encoding the antibody or fragments thereof, specific CDRs and proteins comprising or containing CDRs, vectors containing said DNA and host cells containing said vectors.

Another object of the present invention are the recombinant derivatives of said antibody. In particular, preferred recombinant derivatives are those where the murine constant region is replaced by the human counterpart (Ferrer C. et al. *J. Biotechnol.* 52: 51-60, 1996) or those where the murine constant region is replaced by a biologically active moiety, such as, for example, a member of the avidin family (Manuel L. et al., *J. Immunol.*, 163: 4421-4426, 1999), a growth factor useful for stimulating tumor-directed immunological effectors (such as for example G-CSF, GM-CSF), or those wherein the murine constant region is replaced by a pharmacologically active moiety, such as for example a toxin, a superantigen, a cytokine or any other protein useful in enhancing the antitumor therapeutical efficacy (Di Massimo A. M. et al., *British J. Cancer* 75(6):822-828, 1997; Parente D. et al., *Anticancer Research* 17(6A):4073-4074, 1997).

The methods for obtaining said recombinant derivatives are well-known in the art.

Another object of the present invention are the conjugate derivatives of said antibody.

In particular, preferred conjugate derivatives are those where biologically active moiety are linked to the antibody by way of conventional methods. Examples of biologically active moieties are member of the avidin family, a growth factor useful for stimulating tumor-directed immunological effectors (such as for example G-CSF, GM-CSF), a pharmacologically active moiety, such as for example a toxin, a superantigen, a cytokine or any other protein useful in enhancing the antitumor therapeutical efficacy, antitumor drugs, radioisotopes.

According to the present invention, recombinant derivatives or conjugates of the monoclonal anti-human tenascin or fragments thereof are also indicated as "derivatives".

In a most particularly preferred embodiment of the invention, other than the antibody and the fragments, also the derivatives thereof are biotinylated.

Still another object of the present invention is the hybridoma cell line producing the antibody as above defined. Said hybridoma has been deposited with Advanced Biotechnology Center on 29 Jan. 2002 under the provision of Budapest Treaty, with the number PD02003.

As a further object of the present invention, a process for the preparation of the monoclonal antibody is provided, said process comprising cultivating the above hybridoma cell line and isolating the antibody.

Another object of the present invention is the use of the monoclonal antibody anti-human tenascin for the preparation of a medicament for the treatment of a disease expressing tenascin, in particular a tumor.

A non limiting, exemplary list of tumors expressing tenascin are gliomas, mammary, lung carcinomas, fibrosarcomas and squamous cell carcinomas.

Still another aspect of the present invention is a medicament for the radioimmunotherapy of tumors, which is administered to a subject suffering from a tumor expressing tenascin, and comprises said monoclonal antibody or proteolytic fragments, or derivatives thereof. In a preferred embodiment, said monoclonal antibody or proteolytic fragments or derivatives thereof are biotinylated, in a more particularly preferred embodiment, the medicament is suitable for radioimmunotherapy, in particular for carrying out the three-step pre-targeting method, as described in the art, for example in EP 0 496 074, *European Journal of Nuclear Medicine* Vol. 26, No 4; April 1999; 348-357 and U.S. Pat. No. 5,968,405. In this latter aspect, the medicament according to the present invention shall be in the form of a kit, said kit being composed of 5 vials, whose first vial contains the biotynilated antibody or fragment or derivative thereof; the second vial contains an avidin, the third vial contains biotinylated albumin, the fourth vial contains a streptavidin, the fifth vial contains radiolabelled biotin or biotin derivative. Such a kind of kit is provided in *European Journal of Nuclear Medicine* Vol. 26, No 4; April 1999; 348-357. An avidin comprises avidin, streptavidin, PEG-avidin or PEG-strepatavidin, di- or polyavidin or di- or polystreptavidin. A radiolabelled biotin contains a radionuclide, such as disclosed in EP 0 496 074, preferably 90Y. Biotin derivatives are disclosed, for example in WO 02/066075. A kit of this kind is disclosed in *European Journal of Nuclear Medicine* Vol. 26, No 4; April 1999; 348-357. Preferably, the vials are suitable for human injection.

The recombinant derivatives of the antibody of the present invention, as well as its conjugates are also conveniently used in tumor therapy. Although the antibody of the present invention as well as the fragments, derivatives and conjugates thereof are suitably used in the treatment of tenascin-related tumors, in particular by way of immunotherapy, radioimmunotherapy is a preferred embodiment of the invention.

The specific container, preferably in the form of a vial suitable for injection, comprising the antibody or fragments thereof, in the biotinylated form, is another object of the present invention.

In another embodiment of the present invention, in the therapeutic kit, the biotinylated antibody is combined with other tenascin-specific antibodies preferentially directed towards the A-D fragment. Alternatively, the biotinylated antibody is combined with other tumor specific antibodies. A general teaching of said kind of kit is provided in EP 0 496 074, *European Journal of Nuclear Medicine* Vol. 26, No 4; April 1999; 348-357 and U.S. Pat. No. 5,968,405.

In particular, the present invention also encompasses a container, optionally containing multiple compartments, comprising the biotinylated antibody or fragments or derivatives thereof, buffers and reagents suitable for use in a therapeutic kit for a three-step pre-targeting method.

Another object of the present invention is the use of said monoclonal antibody or fragments, or recombinant derivatives or conjugates thereof or the biotinylated derivative thereof, for the preparation of diagnostic means, for the detection of diseases expressing tenascin, in particular for in vivo imaging of tumor.

In a particular embodiment of the present invention, said monoclonal antibody or fragments or derivatives thereof is used in combination with a second tenascin-specific antibody in a sandwich assay for the production of a diagnostic kit for the determination of the level of circulating tenascin. The sandwich assay is, for example, an ELISA in vitro assay under conditions where said second antibody binds to a second antigenic epitope of tenascin, said in vitro ELISA assay is useful for determining the level of circulating tenascin.

The diagnostic or therapeutic kits comprising the antibody or fragments or derivatives thereof are a further object of the present invention.

These and other objects of the present invention shall be disclosed in detail in the following description also by means of examples and figures.

BRIEF DESCRIPTION OF THE FIGURES

FIG. 1: shows the schematic representation of human tenascin-C, the related recombinant antigenic fragments and reagents, as well as the strategy used to generate a BC-4 like antibody.

FIG. 2: shows the confirmation of the glycosidic nature of ST2146 heavy chain variability by digesting the antibody with a sialidase.

FIG. 3 shows the overall homogeneity of ST2146 opposed to BC4.

FIG. 4 shows Western Blot ST2146 binding to human tenascin epitope compared with the antigenic epitope of BC4 (Lane D is empty).

FIG. 5 shows competitive ELISA where ST2146 strongly competes with BC4 in the binding to human tenascin while ST2077 shows only partial competition. ST2077 is a tenascin specific monoclonal antibody obtained in the procedure to generate ST2146. ST2077 shows similar ST2146 specificity (EGF-like repeat region of human tenascin) but it is directed toward an antigenic epitope only partially interfering with the BC4/ST2146 epitope.

FIG. 6 shows the immunoreactivity of ST2146 by ELISA in comparison to the fully active peak of BC4.

FIG. 7 shows the protocol for biodistribution study of ST2146.

FIG. 8 shows the biodistribution for ST2146 in comparison with BC4 (biot=biotinylated; IR=Immunoreactivity expressed as the amount of antibody to obtain 1.0 O.D. in ELISA).

FIG. 9 shows the tumor/non-tumor ratio for ST2146 in comparison with BC4.

FIG. 10 shows the sequence of ST2146 variable light chain (VL) (SEQ ID NOs: 1 (full length amino acid), 3 (DNA encoding amino acid), 9 (light chain amino acid of CDR1), 10 (light chain DNA of CDR1), 11 (light chain amino acid of CDR2), 12 (light chain DNA of CDR2), 13 (light chain amino acid of CDR3), 14 (light chain DNA of CDR3) and 21 (full length DNA)).

FIG. 11 shows the sequence of ST2146 variable heavy chain (VH) (SEQ ID NOs: 2 (full length amino acid), 4 (DNA encoding amino acid), (heavy chain amino acid of CDR1), 16 (heavy chain DNA of CDR1), 17 (heavy chain amino acid of CDR2), 18 (heavy chain DNA of CDR2), 19 (heavy chain amino acid of CDR3), and 20 (heavy chain DNA of CDR3) and 22 (full length DNA)).

DETAILED DESCRIPTION OF THE INVENTION

ST2146 is obtained from the corresponding hybridoma cell clone cST2146 as given in detail in the following example.

As far as the industrial aspects of the present invention are concerned, the antibody herein disclosed shall be suitably formulated in pharmaceutical compositions or diagnostic kits as normally done in this technical field.

Pharmaceutical compositions are conventional in this field and can be made by the person skilled in the art just based on the common general knowledge. Examples of pharmaceutical compositions are given in the references mentioned in the present invention. The same applies to diagnostic kits. Particularly preferred in the kit for radioimmunotherapy of tumors as disclosed in the above mentioned papers by Paganelli et al. and EP 0 496 074.

Pharmaceutical compositions comprising the antibody and/or a fragment and/or a recombinant derivative and/or a conjugate thereof in admixture with at least one pharmaceutically acceptable excipient and/or vehicle are included in the scope of the present invention.

The following example further illustrates the present invention.

EXAMPLE 1

In order to generate a new hybridoma cell clone with the specificity of BC4 but lacking the expression of non functional light chain, Balb/c mice were immunized with pTn28 E. coli phage lysate. pTn28 is a λgt11 recombinant clone encoding a fragment of the EGF-like repeat of human tenascin previously shown to contain the BC4 epitope (Balza E. et al., 1993). The schematic representation of human tenascin-C, the related recombinant antigenic fragments and reagents, as well as the strategy used to generate a BC-4 like antibody is given in FIG. 1. pTn28 immunized splenocytes were fused to Sp2/0Ag14 non producing myeloma cells by standard method (Cianfriglia M. et al., Methods Enzymol. 121:193210, 1986) and the hybridoma population screened by ELISA on SK-MEL-28 (human melanoma cell line) purified tenascin. Tenascin specific hybridomas were cloned by limiting dilution two times in FCS containing medium and three times in protein free medium (Animal Derived Component Free Medium HyClone, HyQR Perbio). The cST2146/D3d/F6e subclone was finally selected for the production of the cST2146 Master Cell Bank (MCB) and Working Cell Bank (WCB).

The production of the ST2146 Reference Material was done by cultivation of the cST2146 hybridoma cells in 2 L Bioreactor and the stability of the cST2146 Post Production Cell Bank (PPCB) was confirmed by FACS analysis and by Limiting Dilution.

ST2146 is a mouse immunoglobulin of IgG2b/k isotype.

ST2146 proved to be homogeneous for light chain composition as shown by reducing SDS-PAGE analysis which also showed a certain degree of heterogeneity of the heavy chain. This observation was consistent with a variability in O-linked glycosylation as previously reported for the murine IgG2b isotype (Kim H. et al., J. Biol. Chem. 269(16):12345-12350, 1994). Consistency in the pattern of ST2146 heavy chain bands was observed in three different batches obtained from FCS containing culture medium or protein-free medium. Confirmation of the glycosidic nature of ST2146 heavy chain variability was produced by digesting the antibody with a sialidase. ST 2146 was buffer exchanged with a HiTrap desalting column (Amersham-Pharmacia), to 10 mM sodium phosphate buffer containing 150 mM NaCl, pH 6.4. The Mab was concentrated on centricons 100,000 MWCO (Millipore) to a final concentration of about 1 mg/ml and digested with 1.5 U/ml of sialidase (Sigma) for 24 hours at 37° C. The samples were subjected to electrophoresis on 12% polyacrylamide slab gel. Gel staining was done by Coomassie Brilliant Blue. As expected, this digestion resulted in the elimination of the higher molecular weight band (FIG. 2). The overall homogeneity of ST2146 was also confirmed by hydroxylapatite chromatography which showed a single peak for ST2146 opposed to the three peaks observed for BC4 (FIG. 3, wherein, for BC4 the fully functional corresponds to peak 3).

ST2146 binds human tenascin to an epitope strictly related, if not identical, to the antigenic epitope of BC4 as shown by Western Blot (FIG. 4) and competitive ELISA (FIG. 5). In FIG. 5, biotynilated BC4 was mixed with increasing concentrations of BC4, ST2077 or ST2146 as competitors and plated on tenascin coated plates. Binding was measured after addition of HRP-streptavidin and related chromogenic substrate. ST2077 is an antibody recognizing an epitope of tenascin within the EGF-like repeat, partially shared with the BC4 epitope.

The immunoreactivity of the ST2146 was evaluated by ELISA in comparison to the fully active peak of BC4 (peak 3). FIG. 6 shows that the amount of ST2146 to obtain 1.0 OD in optimal antigen concentration ELISA (panel A) is approximately 20 time less than the amount of the fully reactive peak 3 of BC4 and approximately 100 time less than BC4. This difference is dramatically amplified in conditions of antigen limitation as in panel B where only ST2146 maintains a good immunoreactivity.

The affinity of ST2146 was evaluated by BIAcore. The KD of ST2146 resulted of $1.4 \times 10^{-9}$ (Ka $3.0 \times 10^5$; kd $4.1 \times 10^{-4}$). The ST2146 affinity data were compared to BC4 which shows a KD of $4.9 \times 10^{-9}$ (Ka $1.9 \times 10^5$; kd $9.3 \times 10^{-1}$).

The maintenance of immunoreactivity upon biotinylation is a fundamental feature of a monoclonal antibody to be used for pre-targeting. In order to evaluate the behavior of biotinylated ST2146 different antibody:biotin ratios were investigated and the immunoreactivity of the biotinylated antibody measured by ELISA in comparison to BC4 and ST1897, the latter being a tenascin-specific monoclonal antibody with lower affinity. Results in table 1 show that low biotinylation (2-3 biotins/mole) slightly affects immunoreactivity of monoclonal antibodies independently from their affinities. Higher biotinylation, up to 20 biotins/mole is associated to a reduction in immunoreactivity. This reduction is higher the lower is the antibody affinity.

TABLE 1

Biotinylation study on ST2146

| | | % of Immunoreactivity Moles biotin/antibody | | | |
|---|---|---|---|---|---|
| Mab | Affinity (nM) | 2-3 | 3.5-5 | 7-10 | 15-20 |
| ST1897 | 10 | 84.8 +/− 1.3 | 62.3 +/− 12.4 | 26.65 +/− 13.8 | 9.45 +/− 9.26 |
| BC4 | 4.9 | 82.4 +/− 11.5 | 74.4 +/− 9.3 | 67.2 +/− 12.3 | 12.6 |
| ST2146 | 1.4 | 100 | 89.6 +/− 4.39 | 77.63 +/− 8.59 | 52.37 +/− 3.95 |

% of immunoreactivity is the average of 2-3 independent experiments +/− standard deviation.

The affinity of biotinylated ST2146 was measured by BIAcore and resulted substantially maintained no matter the number of biotins linked.

Immunohistochemistry on different tumors (breast, glioma, colon) showed for BC4 and ST2146 similar selectivity.

The pharmacology behavior of the biotinylated ST2146 was addressed to establish the ability to localize to tumor masses. Biodistribution studies of $^{125}$I-labelled ST2146 and BC4 biotinylated antibodies were done in nude mice grafted with tenascin expressing human tumors according to the protocol in FIG. 7. Mice received subcutaneously $4\times10^6$ HT29 human colon carcinoma cells in 0.1 ml of sterile solution. After 15 days, when the tumor mass was approximately 100 mg, groups of 5 mice received intravenously $^{125}$I-labelled BC4, ST2146 or normal mouse immunoglobulins (nMIg) at 10, 2, 0.5 or 0.1 µg/mouse in 0.1 ml of sterile PBS. All antibodies were biotinylated (7-10 biotins/mole) and both ST2146 and BC4 biotinylated Mabs showed an immunoreactivity of about 80%. Each animal received the following amount of CPMs:

| Dose | BC4 | ST2146 | NMIg |
|---|---|---|---|
| 10 µg | 632.000 | 570.000 | 577.000 |
| 2 µg | 555.000 | 639.000 | 624.000 |
| 0.5 µg | 310.000 | 401.000 | 382.000 |
| 0.1 µg | 186.000 | 211.000 | 174.000 |

Results in FIG. 8 show that both BC4 and ST2146 specifically localize to tumor mass. The amount of both antibodies at the tumor site (expressed as the % of injected dose/gram of tissue) is dose-dependent with a trend in higher accumulation for ST2146. Moreover, ST2146 shows a better tumor/non tumor ratio compared to BC4 as shown in FIG. 9.

Kappa light chain variable region was amplified from circularized cDNA using a couple of primers (5'-TGTCAA-GAGCTTCAACAGGA (SEQ ID NO:5), 51-AAGATG-GATACAGTTGGTGC (SEQ ID NO:6)) that anneal to antibody constant region as described in M. Sassano et al., Nucl. Ac. Res. (1994) 22, 1768-1769.

Gamma heavy chain variable region was amplified from circularized cDNA using the following primers: oligo mouse γ2bCH1 GTCACTGACTCAGGGAAGTAGCC (SEQ ID NO:7); oligo mouse γ2bCH3 GCAACGTGAGACAC-GAGGGTCTG (SEQ ID NO:8) that anneal to antibody constant region as described in M. Sassano et al. Nucl. Ac. Res. (1994) 22, 1768-1769.

PCR was performed using the following conditions: 1 min at 94° C., 1.5 min at 60° C., 2 min at 72° C. for 30 cycles.

The amplified fragments were cloned directly in SmaI cut plasmid pUC18. Two clones containing kappa light chain and 4 clones containing gamma heavy chain variable regions were sequenced.

Sequencing was carried out at MWG Biotech, Germany. Both strands were sequenced. No ambiguities were found.

FIG. 10 shows the sequence of ST2146 variable light chain (VL)

FIG. 11 shows the sequence of ST2146 variable heavy chain (VH)

The overall comparative characterization of ST2146 towards BC4 shows that ST2146 has the following characteristics:

BC4-like monoclonal antibody with respect to epitope specificity;
homogeneous with respect to heavy and light chain composition;
heterogeneous with respect to heavy chain glycosylation;
superior to BC4 with respect to immunoreactivity as expected based on BC4 heterogeneity;
about 3 times superior to BC4 with respect to affinity;
superior to BC4 with respect to maintenance of immunoreactivity upon biotinylation;
similar to BC4 for selectivity in immunoistochemistry;
superior to BC4 with respect to tumor targeting.

LIST OF REFERENCES

Balza E., Siri A., Ponassi M., Caocci F., Linnala A., Virtanen I., Zardi L. Production and characterization of monoclonal antibodies specific for different epitopes of human tenascin. FEBS 332:39-43, 1993.

Chinol M., Casalini P., Maggiolo M., Canevari S., Omodeo E. S., Caliceti P., Veronese F. M., Cremonesi M., Chiolerio F., Nardone E., Siccardi A. G., Paganelli G. Biochemical modifications of avidin improve pharmacokinetics and biodistribution, and reduce immunogenicity. British Journal of Cancer 78(2): 189-197, 1998.

Cianfriglia M., Mariani M., Armellini D., Massone A., Lafata M., Presentini L. and Antoni G. Methods for high frequency production of soluble antigen-specific hybridomas; specificities and affinities of monoclonal antibodies obtained. Methods Enzymol 121:193210, 1986.

Cremonesi M., Ferrari M., Chinol M., Stabin M. G., Grana C., Prisco G., Robertson C., Tosi G., Paganelli G. Three-step radioimmunotherapy with yttrium-90 biotin: dosimetry and pharmacokinetics in cancer patients. Eur J Nucl Med 26(2):110-120, 1999.

Di Massimo A M., Di Loreto M., Pacilli A., Raucci G., D'Alatri L., Mele A., Bolognesi A., Polito L., Stirpe F. and De Santis R. Immunoconjugates made of an anti EGF-receptor Monoclonal Antibody and Type 1 RIPs from Saponaria ocymoides or Vaccaria pyramidata. British J. Cancer 75(6):822-828, 1997

Parente D., D'Alatri L., Di Massimo A M., Saccinto M P., Novelli S., Pacilli A., Mele A. and De Santis R. Production and in vitro characterization of a recombinant immunotoxin made of a single chain anti-EGF receptor antibody and a type ribosome-inactivating protein (RIP) from filamentous fungus Aspergillus clavatus. Anticancer Research 17(6A):4073-4074, 1997

Kim H, Yamaguchi Y, Masuda K, Matsunage C, Yamamoto K, Irimura T, Takahashi N, Kato K, Arata Y. O-glycosylation in hinge region of mouse immunoglobulin G2b. J Biol Chem 269(16):12345-12350, 1994.

Ferrer C., Anastasi A. M., Di Massimo A. M., Bullo A., Di Loreto M., Raucci G., Pacilli A., Rotondaro L., Mauro S., Mele A. and De Santis R. Expression and characterization of a mouse/human chimeric antibody specific for EGF receptor. J. Biotechnol. 52: 51-60, 1996

Manuel L. Penichet,* Young-Sook Kang, † William M. Pardridge, ‡ Sherie L. Morrison,* and Seung-Uon Shin An Antibody-Avidin Fusion Protein Specific for the Transferrin Receptor serves as a Delivery Vehihle for Effective Brain Targeting: Initial Applications in Anti-HIV Antisense Drug Delivery to the Brain 1 J Immunol 163: 4421-4426, 1999.

Paganelli G., Grana C., Chinol M., Cremonesi M., De Cicco C., De Braud F., Robertson C., Zurrida S., Casadio C., Zoboli S., Siccardi A. G., Veronesi U. Antibody-guided three step therapy for high grade glioma with yttrium-90 biotin. Eur J Nucl Med 26(4):348-357, 1999.

Paganelli G., Bartolomei M., Ferrari M., Cremonesi M., Broggi G., Maira G., Sturiale C., Grana C., Prisco G., Gatti M., Caliceti P., Chinol M. Pre-targeted locoregional radioimmunotherapy with 90Y-biotin in glioma patients: Phase I study and preliminary therapeutic results. Cancer Biother & Radiopharm 16(3):227-235, 2001.

Parente D., D'Alatri L., Di Massimo A M., Saccinto M P., Novelli S., Pacilli A., Mele A. and De Santis R. Production and in vitro characterization of a recombinant immunotoxin made of a single chain anti-EGF receptor antibody and a type ribosome-inactivating protein (RIP) from filamentous fungus *Aspergillus clavatus*. Anticancer Research 17(6A):4073-4074, 1997

Ramose D. M. Chen B, Regezi J, Zardi L, Pytela R Tenascin-C matrix assembly in oral squamous cell carcinoma. Int J Cancer 75:680-687, 1998.

Siri A., Carnemolla B., Saginati M., Leprini A., Casari G., Baralle F. and Zardi L. Human tenascin: primary structure, pre-mRNA splicing patterns and localization of the epitope recognized by two monoclonal antibodies. Nucl Acid Res 19(3):525-531, 1991.

All references cited or referred to herein are incorporated by reference herein in their entirety.

---

The invention claimed is:

1. A monoclonal antibody to human tenascin C or a fragment thereof, whose light chain variable region comprises the amino acid sequence SEQ ID NO:9, SEQ ID NO:11 and SEQ ID NO:13 and heavy chain variable region comprises the amino acid sequence SEQ ID NO:15, SEQ ID NO:17 and SEQ ID NO:19, or a fragment of said monoclonal antibody, wherein said antibody or fragment binds to an antigenic epitope with the EGF-like repeat of human tenascin C.

2. A conjugate comprising the monoclonal antibody or the fragment of claim 1, said conjugate further comprising at least one marker, diagnostic agent or biotin.

3. The antibody or fragment of claim 1, wherein said antibody or fragment is produced recombinantly.

4. The antibody or fragment of claim 1, which comprises a human constant region.

5. The conjugate of claim 2, wherein said conjugate further comprises a member of the avidin family or a cytokine.

6. The conjugate of claim 2, wherein said conjugate further comprises a toxin, a superantigen or a cytokine.

7. The conjugate of claim 2, wherein said conjugate further comprises an antitumor drug or a radioisotope.

8. A therapeutic kit comprised of five vials, whose first vial contains a conjugate of claim 2, the second vial contains an avidin, the third vial contains biotinylated albumin, the fourth vial contains streptavidin and the fifth vial contains a radiolabelled biotin or biotin derivative.

9. The therapeutic kit according to claim 8, wherein the contents of said vials are suitable for human injection.

10. A method of determining levels of circulating tenascin comprising contact an antibody of fragment of claim 1, said antibody or fragment produced recombinantly, with a second tenascin-specific antibody in a sandwich assay in the presence of a patient sample and determining the level of circulating tenascin.

11. A diagnostic kit comprising the antibody or fragment of claim 1.

12. A container comprising conjugate of claim 2, and a buffer or a reagent.

13. The container according to claim 12, further comprising a separate tenascin-specific antibody which binds the A-D fragment.

14. The container of claim 12 further comprising a separate tumor specific antibody.

15. The antibody of claim 1 in combination with a second tenascin-specific antibody where said second antibody binds to a second antigenic epitope of tenascin.

16. A pharmaceutical composition comprising the antibody or fragment of claim 1 in admixture with at least one pharmaceutically acceptable excipient or vehicle.

17. The conjugate of claim 2, wherein said antibody or fragment is produced recombinantly.

18. The conjugate of claim 2, which comprises a human constant region.

19. The antibody or fragment of claim 1, wherein said fragment is proteolytic.

20. The container according to claim 12, wherein said container contains multiple compartments.

21. A method of determining levels of circulating tenascin comprising contacting a conjugate of claim 2 with a second tenascin-specific antibody in a sandwich assay in the presence of a patient sample and determining the level of circulating tenascin.

22. The container according to claim 13, wherein said tenascin-specific antibody which binds the A-D fragment is in a separate compartment of said container.

23. The container according to claim 14, wherein said tumor specific antibody is in a separate compartment of said container.

* * * * *